United States Patent

Herrin et al.

[11] 4,052,439
[45] Oct. 4, 1977

[54] CARBOXYLIC ESTERS OF PHOSPHONOACETIC ACID

[75] Inventors: Thomas Raymond Herrin, Waukegan; John Scott Fairgrieve, Lake Villa, both of Ill.

[73] Assignee: Abbott Laboratories, North Chicago, Ill.

[21] Appl. No.: 681,874

[22] Filed: Apr. 30, 1976

[51] Int. Cl.² ............ C07D 69/14; A61K 31/22
[52] U.S. Cl. .................. 560/129; 260/403; 424/311; 424/312; 560/263
[58] Field of Search ............. 260/478, 479 R

[56] References Cited
PUBLICATIONS

Kuznetsov et al., Chemical Abstracts, 86262w, vol. 69, 1968.
Lomakina et al., Chemical Abstracts, 15447, vol. 63, 1965.

*Primary Examiner*—James O. Thomas, Jr.
*Assistant Examiner*—Jane T. Fan
*Attorney, Agent, or Firm*—Robert L. Niblack

[57] ABSTRACT

A method of treating herpes simplex infections in warm-blooded animals by administering to said animals a carboxylic ester of phosphonoacetic acid of the formula

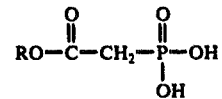
(1)

wherein R is a $C_3$-$C_8$ alkyl, aralkyl,

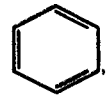

, adamantyl, or glyceryl esters of the formula

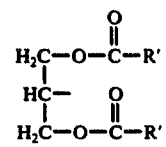

where R' is an alkyl of 2-20 carbon atoms, or its inorganic salts.

7 Claims, No Drawings

CARBOXYLIC ESTERS OF PHOSPHONOACETIC ACID

BACKGROUND OF THE INVENTION

Herpes virus infections, though known, are difficult to treat because of the lack of effective drugs. An effective anti-herpes drug could be used in the treatment or prevention of herpes dermatitis, herpes genitalis, herpes keratitis, herpes encephaltis and as provided by the present invention, herpes simplex virus. Although herpes simplex is a very common, though minor disease, the only basic treatment presently available is the application of idoxuridine.

DETAILED DESCRIPTION OF THE INVENTION

This invention relates to a method of treating the effect of herpes simplex infections in warm-blooded animals comprising administering to such infected animal, a carboxylic ester of phosphonoacetic acid of the structure:

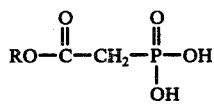
(I)

wherein R is a $C_3-C_8$ alkyl, aralkyl,

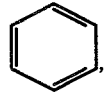

adamantyl, or glyceryl esters of the formula

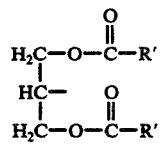

where R' is an alkyl of 2-20 carbon atoms or its inorganic salts.

The ester compounds are active against herpes simplex virus in tissue culture. They are also active in vivo when administered either as the acid or the alkali metal salts, particularly the mono or di sodium, and calcium salts. The compounds are preferably administered topically, but can also be given by the oral or intraperitoneally (i.p.) route.

The present carboxylic esters of phosphonoacetic acid may be prepared by two methods. The two methods (A) and (B) that may be used to produce the carboxylic esters of phosphonoacetic acid are as follows.

METHOD (A)

This method is taken from the procedure described in the publication of G. M. Kosolapoff, "Organophosphorus", John Wiley, N.Y. (1950), p. 160. The general method as used in preparing propyl phosphonoacetate is as follows:

phosphonoacetic acid, 5.0 g., is dissolved in a large excess of 1-propanol. The solution is chilled in an ice bath and saturated with gaseous hydrochloric acid. This solution is then refluxed for 4 hours. The solvent is evaporated at a reduced pressure and the viscous residue dried in vacuo overnight to provide the desired product.

METHOD (B)

This method is, in general, a milder method than Method (A) for the preparation of carboxylic esters of phosphonoacetic acid.

In this method, the chloroacetate of the desired alcohol is treated with tris(trimethylsilyl) phosphite to give the triester of phosphonoacetic acid. The triesters are easily hydrolyzed with water to give the monoesters which are characterized as the ammonium salts. The general method as used in preparing benzyl phosphonoacetate (ammonium salt) is as follows:

A solution of 7.36 g. (0.04 mole) of benzyl chloroacetate and 18.7 g. (0.062 mole) of tris(trimethylsilyl) phosphite was placed in a flask equipped with a distillation head. The flask was heated gradually to 160°-5° C. at which temperature chlorotrimethylsilane is formed and distills. The distillation was complete within about 10 minutes and the solution held at 165° C. for a total of 1 hour. The volatile material in the pot residue was removed by evaporative distillation (air bath temperature 120° C./0.5 mm). The pot residue was evaporatively distilled at 140°-150° C./0.5 mm to give 14.28 g. (83% of benzyl P,P-bis (trimethylsilyl)phosphonoacetate. To 5 g. (0.0116 mole) of the silyl ester was added 20 ml. of water. The mixture was concentrated at reduced pressure and the residue treated with aqueous ammonium hydroxide and the solvent evaporated. The residue was dried by an ethanol azeotrope and the residue crystallized from ethanol to give 1.20 g. (41%) of the mono ammonium salt of benzyl phosphonoacetate.

The carboxylic esters of phosphonoacetate acid of the present invention that may be prepared according to method (A) include:

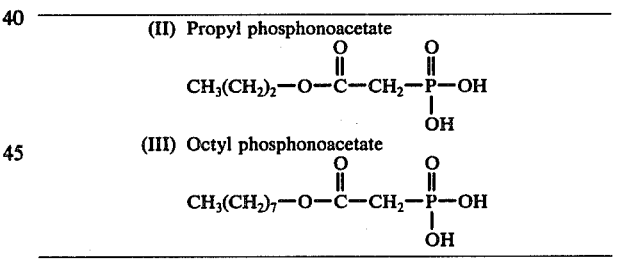

and those made by Method (B) include:

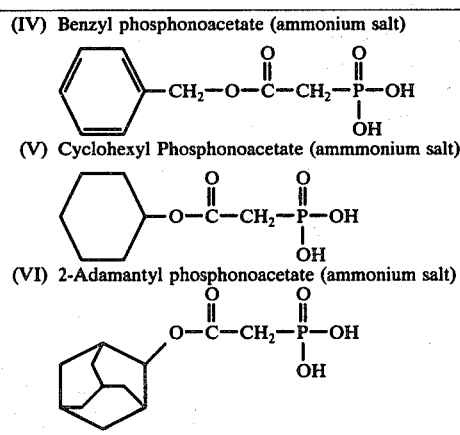

-continued (VII) t-Butyl phosphonoacetate (ammonium salt)

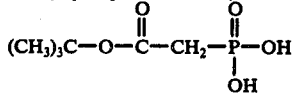

(VIII) 1,3-Dipatmitoxy-2-propyl phosphonoacetate

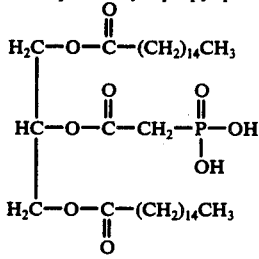

The melting points of the above compounds (i.e., II –VIII) are not able to be definitely determined. The range of the melting points for each compound is too broad to record a characteristic melting point for each compound. In order to identify the compounds, Table I below lists the characteristic Nuclear Magnetic Resonance (NMR) signals of each of the above compounds.

TABLE I
CHARACTERISTIC NMR SIGNALS OF CARBOXYLIC ESTERS OF PHOSPHONOACETIC ACID

| Compound | Solvent | Chemical Shift of Methylene-Phosphorus (ppm from TMS) | Chemical Shift of Additional Signals (ppm from TMS) |
|---|---|---|---|
| IV | DMSO | 2.65 | 5.1(—CO$_2$—CH$_2$—)s 7.35 (Ph—)s |
| V | D$_2$O | 2.85 | 1.6[(CH$_2$)$_5$—]m |
| VI | CDCl$_3$ | 3.00 | 5.00(—CH$_2$CH<)m |
| VII | HOAc | 2.90 | 1.43(t—bu)s |
| II | D$_2$O | 2.75 | 4.05(C—CO$_2$CH$_2$—)t |
| III | CDCl$_3$ | 3.06 | 4.16(—CO$_2$CH$_2$—)t | s = singlet, d = doublet, t = triplet, m = multiplet
TMS = tetramethylsilane, DMSO = dimethyl sulfoxide, D$_2$O = deuterium oxide, CDCl$_3$ = deuterochloroform, HOAc = acetic acid The following examples further illustrate the present invention.

EXAMPLE 1

Cyclohexyl Phosphonoacetate Monoammonium Salt

A solution of 7.04 g. (0.04 mole) of cyclohexyl chloroacetate and 18.0 g. (0.06 mole) of tris(trimethylsilyl) phosphite was heated at 170° for 1 hour. The residue was evaporatively distilled to give 14.52 (98%) of cyclohexyl P,P-bis(trimethylsilyl)phosphonoacetate (air bath temperature 130° C./0.5 mm). To 10 g. (0.0271 mole) of the above silyl ester H$_2$O was added. The mixture was evaporated and the residue treated with ammonium hydroxide and the salt crystallized from C$_2$H$_5$OH to give 4.15 g. (63%) of product.

Analysis Calcd. for: C$_8$H$_{18}$NO$_5$P; C, 40.17; H, 7.58; N, 5,85;
Found: C, 39.97; H, 7.87; N, 5,73.

EXAMPLE 2

2-Adamantyl Phosphonoacetate Monoammonium Salt

A solution of 9.16 g. (0.04 mole) of 2-adamantyl chloroacetate and 15.0 g. (0.05 mole) of tris(trimethylsilyl) phosphite was heated at 160° C. for 1 hour. The volatile material was evaporatively distilled to give 16.14 g. of residue. The residue, 10.0 g. (0.023 mole), was treated with H$_2$O and then NH$_4$OH to give, after crystallization from C$_2$H$_5$OH, 4.2 g. (62% of product, m.p. 222°–224° C.

Analysis Calcd. for C$_{12}$H$_{19}$O$_5$P.O. 82 NH$_3$; C, 50.00; H, 7.50; N, 3.99;
Found: C, 49.94; H, 7.46; N, 3.95.

EXAMPLE 3

1,3-Dipalmitoxy-2-Propyl Phosphonacetate

A solution of 5.05 g. of 1,3-dipalmitoxy-2:propyl chloroacetate and 6.0 g. (0.02 mole) of tris(trimethylsilyl) phosphite was heated at 190°–200° C. for 1.5 hours. The volatile material was evaporatively distilled and the residue treated with H$_2$O. The precipitate was dried and crystallized from (C$_2$H$_5$)$_2$O to give 4.05 g. of product, m.p. 81.5° –83.0° C.

Analysis Calcd. for C$_{37}$H$_{71}$O$_9$P: C, 64.32; H, 10.36;
Found: C, 63.78; H, 10.55.

EXAMPLE 4 t-Butyl Phosphonoacetate Ammonium Salt

A solution of 6.0 g. (0.04 mole) of t-butyl chloroacetate and 18.0 g. (0.06 mole) of tris(trimethylsilyl) phosphite was heated at 165–170° C. for 2 hours. The residue was distilled, b.p. 104° –108° C./0.5 mm to give t-butyl P,P-bis(trimethylsilyl)phosphonoacetate. The latter compound was hydrolyzed with H$_2$O and converted to its ammonium salt. The yield was 2 g.

Analysis Calcd. for C$_6$H$_{19}$N$_2$O$_5$P: C, 31.30; H, 8.32; N, 12.17;
Found: C, 30.70; H, 8.50; N, 12.10.

EXAMPLE 5

Octyl Phosphonoacetate

Hydrochloric acid was passed through a solution of 5 g. of phosphonoacetic acid and 1-octanol for 0.5 hours. The solution was heated (100° C.) for 4 hours. The solvent was evaporated and the residue dried under vacuum to give 5 g. of product.

Analysis Calcd. for C$_{10}$H$_2$O$_5$P. ½ H$_2$O; C, 45.97; H, 8.49;
Found: C, 46.24; H, 8.40.

EXAMPLE 6

Herpes Simplex Viruses

Isolation and Purification of Herpes Simplex Type 2 Deoxyribonucleic Acid (DNA) Polymerase herpes virus infected Wi-38 cells were grown and harvested when 25% of the cells showed cytophathic effect of the virus. The DNA polymerase was isolated according to the procedure of Smith and Gallo (1972) which involved column chromatography on DEAE-cellulose and phosphocellulose. However, buffer containing 20% glyceryl instead of 10% was used. The final enzyme preparation has a specific activity of 313 units/mg. for herpes simplex virus type 2.

Viral Deoxyibonucleic Acid (DNA) Polymerase Assay

The reaction mixture (0.2 ml.) contains 10 μM of 2'-deoxyadenosine-5'-triphosphate, 2'-deoxycytidine-5'-triphosphate, 2'-deoxyguanosine-5'-triphosphate, and 2.5 μM tritium labeled thymidine-5'-triphosphate which was appropriately diluted with unlabeled dTTP to give 880 counts per minute per pico-mole, 10 μg of activated calf thymus DNA 50 mM Tris-HCl buffer (pH 8.0), 3mM MgCl$_2$, 100 mM KCl and 1 mM dithiothritol. The amounts of enzyme used in each reaction was chosen to give a linear rate for at least 30 minutes at 37° C. The reaction was terminated by the addition of 3 ml. of cold 5% trichloroacetic acid - 0.01 M sodium pyrophosphate. The acid-insoluble material was collected, washed twice on glass filter discs (Reeve Angel 984-H) and the incorporated $^3$H-dTMP was determined by a liquid scintillation counter.

The effect of each of the compounds in the inhibition of viral deoxyribonucleic acid (DNA) polymerase in mice is recorded below in Table II.

TABLE II

| INHIBITION OF VIRAL DNA POLYMERASE (%) | | |
|---|---|---|
| Compound | Concentration (μg/ml) | Percent Inhibition |
| II | 4.7 | 50% |
| III | 15.0 | 50% |
| IV | 40.0 | 50% |
| V | 49.0 | 50% |
| VI | 166.0 | 50% |
| VII | 4.0 | 50% |
| VIII | 166.0 | 73% |

EXAMPLE 7

The effectiveness of a carboxylic ester of phosphonoacetic acid against herpes simplex infections in mice was determined as follows.

Mice were infected with herpes simplex, virus, type 2 and treated with the carboxylic ester two hours post infection and each of the five days thereafter. Virus inoculation was accomplished by plucking the fur from the flank and back of anesthetized mice and placing a top (0.05 ml.) of herpes virus on the surface of the plucked skin. Using a needle, the skin of the mouse was pricked through a drop of virus. The mice utilized for control purposes were not treated in any manner.

The average survival of untreted, infected mice was 9.1 days. the mice treated topically (2% aqeuous solution) with compound II (of Tables I and II above) had a survival time of 11.8 days (P = 0.05)*

We claim:

1. A carboxylic ester of phosphonoacetic acid of the formula

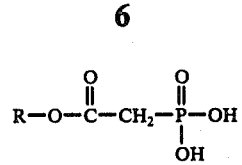

wherein r is $C_3-C_8$ alkyl, aralkyl,

or adamantly.

2. A carboxylic ester according to claim 1 wherein R is $CH_3(CH_2)_2-$.

3. A carboxylic ester according to claim 1 wherein R is $CH_3(CH_2)_7-$.

4. A carboxylic ester according to claim 1 wherein R is

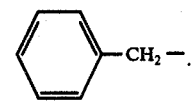

5. A carboxylic ester according to claim 1 wherein R is

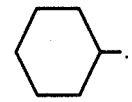

6. A carboxylic ester according to claim 1 wherein R is

7. A carboxylic ester according to claim 1 where R is $(CH_3)_3C-$.

* * * * *

*Statistical analysis using the Mann-Whitney U test.